US010620191B2

(12) United States Patent
Stöcker et al.

(10) Patent No.: US 10,620,191 B2
(45) Date of Patent: Apr. 14, 2020

(54) TESTKIT FOR LABORATORY DIAGNOSTICS

(71) Applicant: Euroimmun Medizinische Labordiagnostika AG, Lübeck (DE)

(72) Inventors: Winfried Stöcker, Gross Grönau (DE); Wolfgang Meyer, Pansdorf (DE); Thomas Scheper, Berkenthin (DE); Antje Euken, Lübeck (DE)

(73) Assignee: Euroimmun Medizinische Labordiagnostika AG, Lübeck (DE)

( * ) Notice: Subject to any disclaimer, the term of this patent is extended or adjusted under 35 U.S.C. 154(b) by 1324 days.

(21) Appl. No.: 13/886,952

(22) Filed: May 3, 2013

(65) Prior Publication Data

US 2014/0186971 A1 Jul. 3, 2014

(30) Foreign Application Priority Data

May 3, 2012 (DE) .................... 20 2012 004 404 U

(51) Int. Cl.
| | |
|---|---|
| *G01N 33/53* | (2006.01) |
| *G01N 33/558* | (2006.01) |
| *G01N 33/543* | (2006.01) |
| *B01L 3/00* | (2006.01) |
| *G01N 35/00* | (2006.01) |

(52) U.S. Cl.
CPC ...... *G01N 33/5302* (2013.01); *B01L 3/50855* (2013.01); *G01N 33/54386* (2013.01); *G01N 33/558* (2013.01); *B01L 2200/028* (2013.01); *B01L 2300/044* (2013.01); *B01L 2300/0825* (2013.01); *G01N 2035/00108* (2013.01); *G01N 2035/00346* (2013.01)

(58) Field of Classification Search
CPC ............ G01N 33/564; G01N 2333/20; G01N 2469/20; G01N 33/6911; G01N 1/2813; G01N 1/312; G01N 2021/7786; G01N 21/0332; G01N 21/274; G01N 21/6456; G01N 21/7703; G01N 2035/00108; G01N 33/5302
See application file for complete search history.

(56) References Cited

U.S. PATENT DOCUMENTS 4,859,419 A * 8/1989 Marks et al. ................. 422/417
5,009,316 A * 4/1991 Klein ....................... B01L 9/06
                                                  206/443
(Continued)

FOREIGN PATENT DOCUMENTS

EP            0720020 A1 *  7/1996   ............. G01N 33/53

*Primary Examiner* — Changhwa J Cheu
(74) *Attorney, Agent, or Firm* — Grüneberg and Myers PLLC

(57) ABSTRACT

A device for incubating an immunoblot strip (6) includes at least one incubation channel (1) into which an elongate immunoblot strip (6) having at least one biological material on its front is inserted with its back facing a channel base (2). An agitating means (7), with which the immunoblot strip (6) is agitatable around a transverse axis (8) of the strip (6) at least at times during incubation via an agitating device (7). For handling and/or grouping incubation channels (1) with immunoblot strips (6) inserted, a rack (3) for taking up at least two incubation channels (1) is provided. The rack (3) is in operative connection with said agitating means (7) via load transmission points.

13 Claims, 3 Drawing Sheets

(56) References Cited

U.S. PATENT DOCUMENTS

| | | | | |
|---|---|---|---|---|
| 5,567,595 A * | 10/1996 | Kok | ............... | G01N 33/54366 |
| | | | | 422/536 |
| 6,558,631 B1 * | 5/2003 | Day | ................ | B01L 3/5085 |
| | | | | 206/538 |
| 7,708,946 B1 * | 5/2010 | Sherman et al. | ............... | 422/63 |
| 8,961,908 B1 * | 2/2015 | Bommi | ............... | B65D 1/34 |
| | | | | 220/516 |
| 2007/0237687 A1 * | 10/2007 | Sleeper | ............... | 422/104 |
| 2010/0025266 A1 * | 2/2010 | Landeta Elorz et al. | ..... | 206/204 |
| 2010/0124750 A1 * | 5/2010 | Stocker et al. | ............... | 435/6 |
| 2014/0113316 A1 * | 4/2014 | Mazzeo | ............... | 435/7.24 |

\* cited by examiner

TESTKIT FOR LABORATORY DIAGNOSTICS

The instant application should be granted the priority date of May 3, 2012, the filing date of the corresponding German patent application DE 20 2012 004 404.4.

BACKGROUND OF THE INVENTION

In the field of medical laboratory diagnostics, different test systems are known, using which patient samples are tested for the presence of special antibodies. With the detection of special patient antibodies and their categorization in certain immunoglobulin classes, it is possible to draw conclusions about bacterial or viral infections, which have occurred or are still present, as well as about the chronological sequence of an infection. Typically, detection of antibodies takes place by way of so-called stepwise diagnostics, in which first sensitive screening is undertaken, followed by a specific confirmation. In that, in routine serology, ELISA (Enzyme-Linked Immunosorbent Assay) is frequently used for screening, while as the confirmation test, immunoblot strips, in particular Western blot strips, dot blot strips or line blot strips, are predominantly used.

For incubation of the various known immunoblot strips, typically so-called blot trays are used, which have a plurality of channels, into which the respectively required blot strips are inserted at the laboratory. Incubation takes place within the channels by filling reagents into the respective channels with the blot strips in the order specified for that. Subsequently, the tray is preferably agitated, so that good intermixing of the reagents and sufficient incubation of the blot strips take place. Following incubation, the strips are first purified using a washing liquid, and subsequently the banding patterns of the individual strips are analyzed. The analysis is normally performed automatically, wherein the incubated blot strips are recorded with a camera or a scanner system, and the recorded images are analyzed with the aid of laboratory software.

In this connection, a blot membrane is known from DE 202 15 268 U1, which is provided with a reversible adhesive on its back. In this case, the reversible adhesive enables fixation of the membrane directly at the base of an incubation channel, whereby turning over of the membrane by filling, emptying or agitating of the incubation channel or the incubation tray during incubation is reliably prevented. In that, the reversible adhesive is optionally applied across the entire dimension of the respective back of the blot membrane or only in a limited area.

Furthermore, DE 202 15 270 U1 discloses very special immunoblot strips, on which different types of test strips are provided. Sections of Western blot strips are combined with line blots, with which a specifically selected antigen can be respectively detected.

Based on the blot strips known from the state of the art and the available means for incubating the strips, the invention is based on the object of creating a process in which the tests using blot strips can be performed comfortably and at the same time, is particularly flexible. In particular, the combination of different antibody detection methods and/or simultaneous testing of various patient serums in the course of a joint incubation process are enabled in a simple manner. Furthermore, with the device according to the present invention, storage, transport, and in particular provision of the individual blot strips can be undertaken reliably and in a very user-friendly manner. Above all, the user is to be enabled to perform incubation sequences, in which, in a simple manner, different blot strips can be combined with one another. The effort to combine different blot strips is minimized. Furthermore, it is to be ensured with relatively simple means, that incubation of the immunoblot strips takes place effectively and reliably, wherein in particular floating or distortion of the test strips are prevented with simple means.

SUMMARY OF THE INVENTION

The above object is solved with a device according to the present invention, specifically, a device for incubating an immunoblot strip with at least one incubation channel, into which an elongate immunoblot strip having at least one biological material on its front has been inserted with its back surface facing a channel base, and with an agitating means, with which the immunoblot strip is agitatable around a transverse axis of the strip at least at times during incubation, has been further developed such that for handling and/or grouping incubation channels with immunoblot strips inserted, a rack to take up at least two incubation channels is provided, and the rack is in operative connection with the agitating means via load transmission points.

Using the technical solution according to the invention, it is possible, in a relatively simple manner, to combine different incubation channels, which preferably have already been provided with an immunoblot strip, into a group, which is moved and incubated jointly. Particularly advantageous is the use of a rack, which is designed in the shape of a frame or tray, wherein the frame or the tray has defined spaces to take up the incubation channels. Thus, the incubation channels required for incubation can be arranged in a frame or on a tray as needed, wherein the incubation channels are reliably held in their positions by suitable locking aids, such as in the form of webs. In particular for incubating immunoblot strips using automatic laboratory equipment, the rack provided according to the invention, which on the one hand serves to take up the incubation channels, and on the other hand is designed and arranged in an agitatable manner, can be used with particular advantage. In this case, in a particularly advantageous manner, different incubation channels or incubation channels which have already been equipped with different blot strips, respectively, can be combined in a group as needed and placed in a frame-shaped rack or on a placement area of automatic laboratory equipment for incubation.

In a preferred embodiment of the invention, a holding element for fixing the blot strip is provided in the incubation channel. The holding element is designed such that the immunoblot strip is securely held in its originally intended position and location, and in particular falling out, distortion, floating or any similar movement is reliably avoided during incubation. Thus, the immunoblot strip is securely fixed within the incubation channel. In an advantageous manner, this holding element is designed as a locking catch or like a holding clamp, respectively, in the area of the channel base. During insertion of an immunoblot strip into the incubation channel, the immunoblot strip is slid under such a locking catch or holding clamp in certain areas, and in this manner fixed within the channel.

Preferably, a multitude of locking catches are provided in the area of the channel base, so that a blot strip can be clamped and thus fixed in this area without damaging it. It is likewise conceivable that the holding element is designed in the shape of a clip, at which a blot strip can be fastened at least in sections. In any case, it is reasonable for the holding element to be designed such that a blot strip can be easily removed from the incubation channel without destroying it. In particular following incubation, but also in case of an equipment error being noticed, this is of high significance.

Additionally, it is conceivable that an adhesive is provided on the back of an immunoblot strip. Preferably, the adhesive is a pressure sensitive adhesive, which enables at least almost residue-free removal and re-adhesion of the blot strip. In an advantageous manner, such a pressure sensitive adhesive on the back of the blot strip guarantees, on the one hand, that also during incubation, shifting, distortion and/or floating of the blot strip is reliably prevented, and on the other hand, that the blot strip can be removed from the incubation channel in a simple manner for later analysis of the test. The adhesive preferably is liquid-resistant, so that undesired detachment of the blot strip from the wall of the incubation channel is also reliably avoided during and after incubation.

Furthermore, it is conceivable to fix the test strip removed from the incubation channel at another surface than the channel base using the pressure sensitive adhesive provided on its back. In a suitable manner, for analysis, such blot strips are adhered to analysis sheets in a specified order in order to scan the surface of the blot strips and to transmit the scan to electronic laboratory software for analysis and diagnosis by a doctor.

In a further special embodiment of the invention, a covering element, in particular a plastic sheet, is provided, which at least at times seals off the incubation channel with the blot strip located therein against the environment. Furthermore, according to a further development, the covering element is fastened to the incubation channel at least in certain areas and entirely covers the channel such that an interior space of the incubation channel with the blot strip located therein is sealed off against the environment.

Alternatively, or in addition, packaging, for example in the form of a bag or package, is provided, in which the incubation channel with the blot strip fixed therein is stored and/or transported. In order to keep the immunoblot strips dry, the packaging is optionally designed such that the immunoblot strip is enclosed airtight by a sheet together with a desiccant, or the blot strip is sealed off using a water-vapor-permeable sheet and the desiccant is located on that side of the sheet opposite the blot strip.

Preferably, the packaging is designed airtight. Such a technical solution is characterized in that the incubation channel forms a unit sealed off against the environment with the blot strip respectively arranged therein.

A very special embodiment of the invention provides that the incubation channels are stackable in a suitable manner. Preferably, at least two channels can be stacked into one another, so that the upper incubation channel slides into the lower channel at least in certain areas. According to a suitable further development, the channels have a conical contour, so that the upper channel does not touch the blot strip in the lower channel once the upper channel has slid into the lower one. Preferably, the incubation channels are furthermore designed such that, following stacking, the upper channel forms a cover in relation to the lower channel. In this case, the blot strip fixed in the lower incubation channel is sealed off against the environment by the upper incubation channel.

According to a preferred embodiment of the invention, at least two elongate incubation channels arranged in parallel to one another are provided, which at their longitudinal sides have a connection area. It is conceivable that the connection area is a closed area, or connection webs are provided in sections only. In a particularly preferred manner, it is conceivable that the connection area between two incubation channels has a perforation, a predetermined breaking point, diminished material strength and/or a notch. A connection area designed such ensures that the at least two incubation channels connected with one another via the connection area can be easily separated from one another, without damaging the incubation channels in doing so. In this connection, it is particularly important that any damaging of the tray-shaped area of the incubation channel, in which incubation of the blot strip takes place, is reliably excluded.

If a packaging unit for test kits designed according to the invention includes a multitude of incubation channels, which are respectively filled with a blot strip, covered by a covering element and connected with one another via a connection area, then, due to a suitable design of the connection area, it is possible to remove individual or groups of immunoblot strips from the packaging unit, without damaging an incubation channel or a covering element such that a blot strip accidentally gets in contact with the environment. In particular, in this manner, particularly simple provision and portioning of the required immunoblot strips is guaranteed.

In a preferred manner, separation of at least one incubation channel from an adjacent incubation channel takes place by also separating the covering elements respectively covering the adjacent incubation channels from one another. Preferably, in this case, the covering element also has a perforation, a predetermined breaking point, diminished material strength and/or a notch in a connection area between the longitudinal sides of two adjacent incubation channels. Alternatively, it is conceivable that each incubation channel, no matter whether it is connected with another adjacent channel, has a separate covering element, wherein the covering elements of adjacent incubation channels in this special case are not connected with one another.

A special further development of the invention furthermore provides that the connection or the connection area, respectively, between two adjacent incubation channels is exclusively formed by covering elements covering the incubation channels with the blot strips located therein. Preferably, it is conceivable that the covering elements of adjacent incubation channels are designed in one piece, and a perforation, a predetermined breaking point, diminished material strength and/or a notch is provided in the connection area between the incubation channels in order to separate the adjacent incubation channels from one another in a suitable manner. Preferably, the covering element is a sheet, more preferred a plastic sheet, which covers at least two adjacent incubation channels. Here, too, the incubation channels with the blot strips located therein are reliably sealed off against the environment, so that in particular contamination, damaging and/or inadmissible moistening of the blot strip are avoided.

According to a further special embodiment of the invention, at least one fastening element is provided at a longitudinal side of the incubation channel, via which the incubation channel can be connected with the take-up rack, in particular in the form of a frame or tray, a further incubation channel, handling equipment, automatic incubation equipment and/or an analysis apparatus. In this connection, it is conceivable that a support area is provided in the circumferential area of an incubation channel at least in sections, so that this channel is particularly easy to place in handling equipment, automatic incubation equipment and/or an analysis apparatus using a frame- or tray-shaped take-up. Furthermore, a special embodiment provides that the fastening element has at least one snap and/or clip connection. Essential in the design of the fastening element is that the incubation channel can be connected with one of the devices stated above, in particular the take-up rack, in a relatively simple manner and in particular without the aid of a tool.

In a very special embodiment of the invention, an incubation channel and/or an incubation tray, which has at least two incubation channels designed according to the invention, is inserted in a frame- or tray-shaped take-up rack by placing the edge area(s) of the channels on respective supports, for example the upper boundary surfaces of intermediate webs. Preferably, incubation takes place with an agitating motion at least at times and/or analysis takes place while the incubation channel or the incubation channels are located within the take-up rack.

According to another further development, it is conceivable that using a suitable fastening element, an incubation channel can be connected with at least one further incubation channel by plugging these together in the area of the fastening elements. This technical variant offers the possibility to connect a different number of and/or even different test strips, i.e. incubation channels with different blot strips, for one test run or one incubation and/or washing step, respectively, with one another, and to place them on or in an agitatably arranged rack.

In a special embodiment of the invention, the antigen provided on the blot strip includes a biological molecule, which can be specifically detected using binding to an antibody. Preferably, a protein, a lipid, a nucleic acid (DNA/RNA), a carbohydrate, a complex molecule and/or an allergen is provided as the antigen. The type of biological material used as the antigen on the blot strip primarily depends on the examination of a patient, which is to be performed using a suitable in vitro examination of a body fluid of the patient.

Preferably, the blot strip is a line blot and/or a Western blot strip. The invention is in particular suited for test runs, in which a multitude of incubation channels with immunoblot strips is combined in or on a frame- or tray-shaped rack. With a combination of several incubation channels with blot strips inserted, in a particular manner, increases in efficiency for provision, incubation and analysis of immunoblot strips are possible.

BRIEF DESCRIPTION OF THE DRAWINGS

In the following, the invention is explained in more detail, without restriction of the general inventive concept, referring to the figures.

FIG. 4: A tray partially equipped with incubation channels; as well as

DETAILED DESCRIPTION OF THE PREFERRED EMBODIMENTS

With the technical solution explained in more detail in the following, effective and time-saving grouping, provision, handling and incubation of a multitude of immunoblot strips 6 can be enabled in a relatively simple manner.

Figure 1:
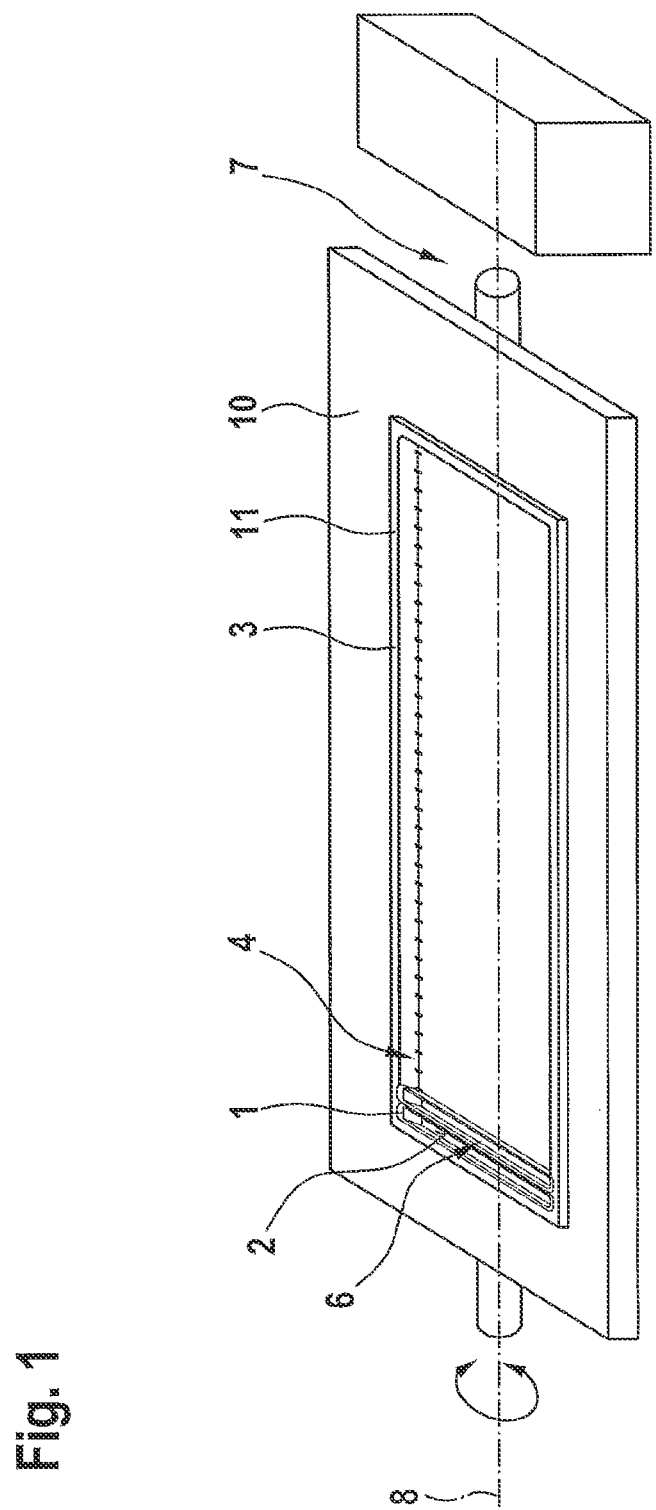
FIG. 1: A device for incubating immunoblot strips with agitating equipment and a tray-shaped rack for taking up the incubation channels.

FIG. 1 shows a device for incubating immunoblot strips 6. Essential in this device is agitating equipment 7 with an platform 10, on which a tray-shaped rack 3 is arranged, which for its part has take-ups 4 arranged next to one another, into which the incubation channels 1, in a preferred manner pre-equipped incubation channels 1, can be inserted. During incubation, the elongate incubation channels 1 are agitated around their transverse axis 8 at least at times, so that the immunoblot strips 6 located therein are brought in close contact with the reagent respectively located in the channel 1. The individual take-ups 4 of the tray-shaped rack 3 are separated by webs 9, between which the incubation channels 1 are securely fixed.

The agitating equipment 7 has an agitatable platform 10, on which the tray-shaped rack 3 with the incubation channels 1 is placed, so that together with the platform 10, the tray-shaped rack 3, the incubation channels 1 as well as the immunoblot strips 6 located therein can also be agitated during incubation. In order to securely fix the individual immunoblot strips 6 within the incubation channels 1, and thus to prevent in particular shifting, distortion as well as floating of the strips, holding elements 5 in the form of clips are provided at the channel bases 2 of the incubation channels 1, under which the strips 6 can be clamped. Clamping takes place such that the incubation strips 6 can be removed from the incubation channel 1 following incubation or in another case of need, without damaging the strips 6.

Figure 2:
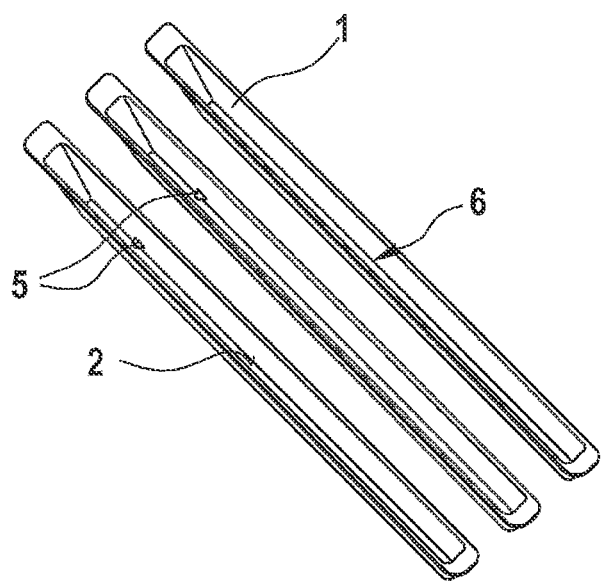
FIG. 2: A perspective view of several individual incubation channels.

FIG. 2 furthermore shows three incubation channels 1 arranged in parallel next to one another in a perspective diagonal top view. The channels 1 are designed such that immunoblot strips 6, which preferably have a pressure sensitive adhesive on their back surfaces, one the one hand, can be securely fixed, and on the other hand, can be easily detached again. The area of the channel base 2 is only marginally larger than the surface of the respectively inserted immunoblot strips 6. In this manner, it is ensured that the amount of a reagent required for optimal incubation and/or a washing liquid can be minimized.

In this view, on the upper front of the incubation channels 1, the channel wall is slightly leveled compared to the opposite side in order to enable relatively easy incubation, in particular comfortable introduction of fluid into the channels 1. Furthermore, in one point in the area of the channel base 2, small clips or locking catches are integrally shaped in the channels 1 as holding elements 5. These clips or locking catches, respectively, ensure that blot strips 6 inserted into the incubation channels 1 "engage" with the catches, and thus subsequently, shifting, distortion and/or floating of the strips 6 during incubation is effectively prevented. Thus, the strips 6 can be securely fixed, independent of whether a pressure sensitive adhesive is applied to the bottom or back, respectively, of the blot strips 6. This again enables that already pre-equipped incubation channels 1, i.e. channels with an immunoblot strip 6, can be produced at the manufacturer's and delivered this way. In this case, the working step of equipping the incubation channels 1 with the immunoblot strips 6 is then no longer required at the laboratory.

At the side of the incubation channels 1 open to the top, these have a flat edge along the entire circumference of the channels 1. With the provision of such an edge, the respective channels 1 can be easily and precisely inserted into respective take-ups 4 of the rack 3 and thus directly or indirectly connected with handling equipment, automatic incubation equipment, analysis units or other laboratory equipment. The edges of the incubation channels 1 then rest on suitable support areas, so that the respective channel 1 is securely held, even if this, in particular during incubation, is moved or agitated, respectively.

Figure 3:
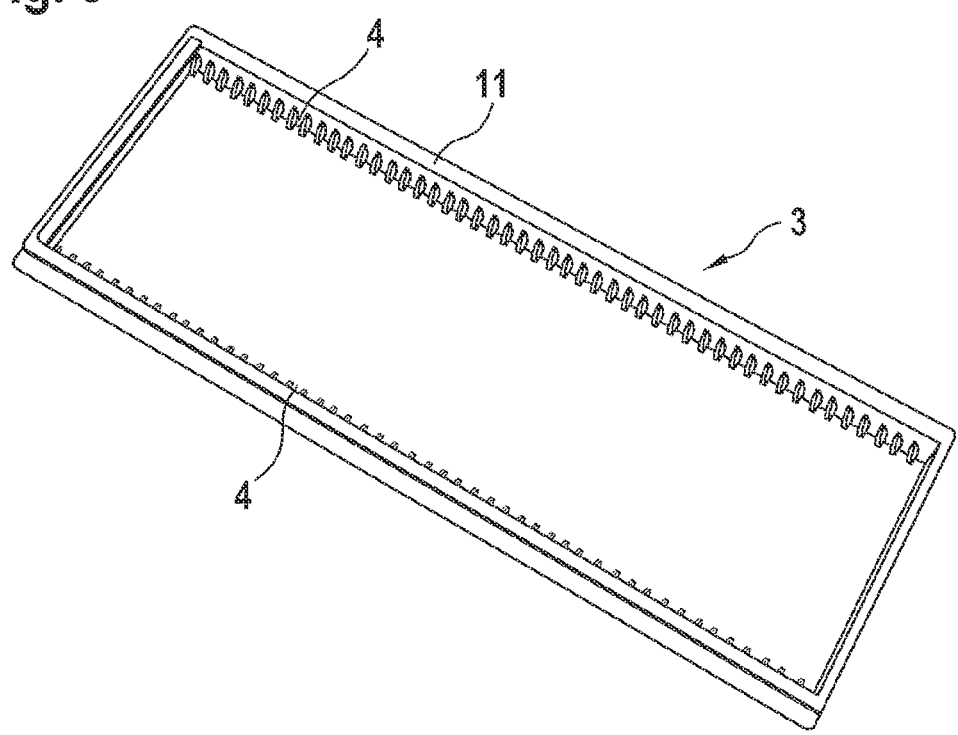
FIG. 3: A tray suited to take up one or several incubation channels.

In addition to the incubation channels 1 shown in FIG. 2, FIG. 3 shows a tray-type rack 3 designed in a suitable manner. This tray 3, which serves take up of at least one, preferably a multitude of incubation channels 1, is designed tray-shaped and has a flat, slightly outwardly protruding edge 11, which, for example, could be positioned on a support area of automatic laboratory equipment. It is likewise conceivable to place such a tray-type rack 3 with its bottom on a platform 10, with which the rack 3 as well as the incubation channels 1 with the immunoblot strips 6 arranged therein are agitated during incubation.

Small webs 9 are provided at the longitudinal sides of the respectively shaped trays 3. The webs 9 are designed and dimensioned such that incubation channels 1, like those shown, for example, in FIG. 2, can be inserted into the intermediate spaces 4 between the webs 9, and hereby slight clamping of the channels 1 is caused. Here, too, it is essential that the channels 1, on the one hand, are securely fixed between the webs 9, and on the other hand, can also be easily removed from the tray 3 again.

The tray 3 as well as the incubation channels 1 are made of a suitable plastic, wherein in particular the tray 3 can be used repeatedly. In the base area, the tray 3 shown in FIG. 3 is designed such that it can be placed on a level surface, like a table or a support of automatic laboratory equipment. It is self-evident that trays 3 can be manufactured in different sizes as needed, so that depending on the tray size, a different number of incubation channels 1 and/or incubation trays, which have at least two connected incubation channels 1, can be arranged on the tray 3. In respect of automatic laboratory equipment, it is likewise conceivable that equal or different trays 3 are placed into the respective racks, take-up frames and/or on support plates provided for that.

Figure 4:
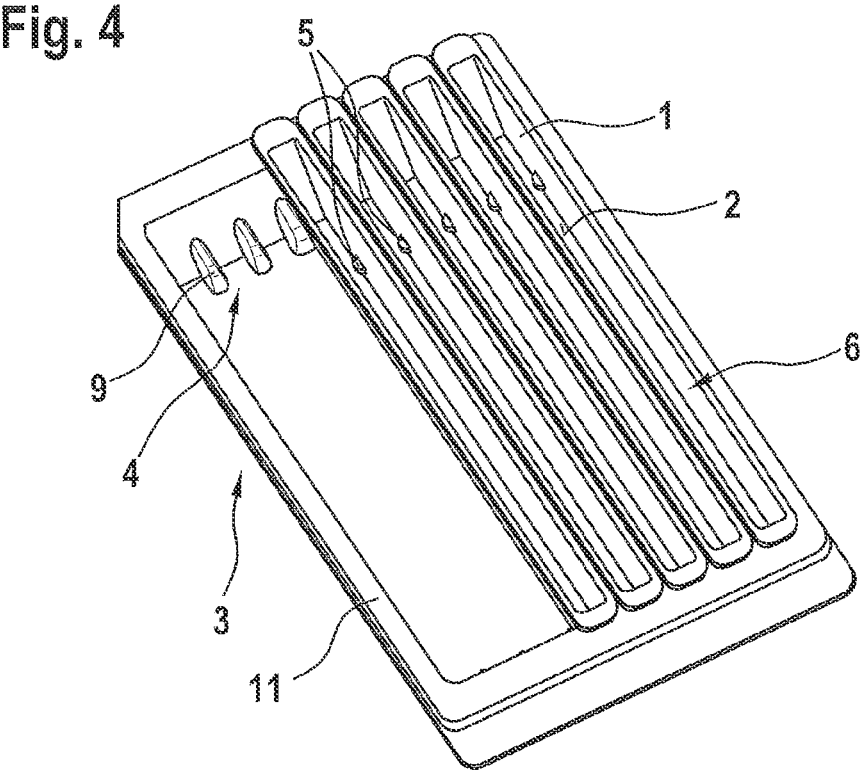

FIG. 4 shows a respectively shaped tray 3 with the webs 9 and a circumferential edge 11 on the outside explained in connection with FIG. 3, which is equipped with five individual incubation channels 1. The channels 1 were inserted into the take-ups 4 provided for that and are fixed by the webs 9. In the embodiment shown, three further take-up areas 4 suitable for fixing incubation channels 1 have not been equipped with channels 1.

Within the individual incubation channels 1, oppositely disposed clips 5 are provided in the base area 2, with which an immunoblot strip 6 inserted into the channels 1 is securely held at the base, and thus shifting, distortion and/or floating during incubation is prevented. The number as well as the design and arrangement of the individual clips 5 are always selected such that secure fixing of the immunoblot strips 6 in the channels 1 is guaranteed. Self-evidently, it is conceivable to already equip the channels 1 with blot strips 6 prior to delivery to the laboratories and/or to already place the incubation channels 1 in the tray 3.

Figure 5:
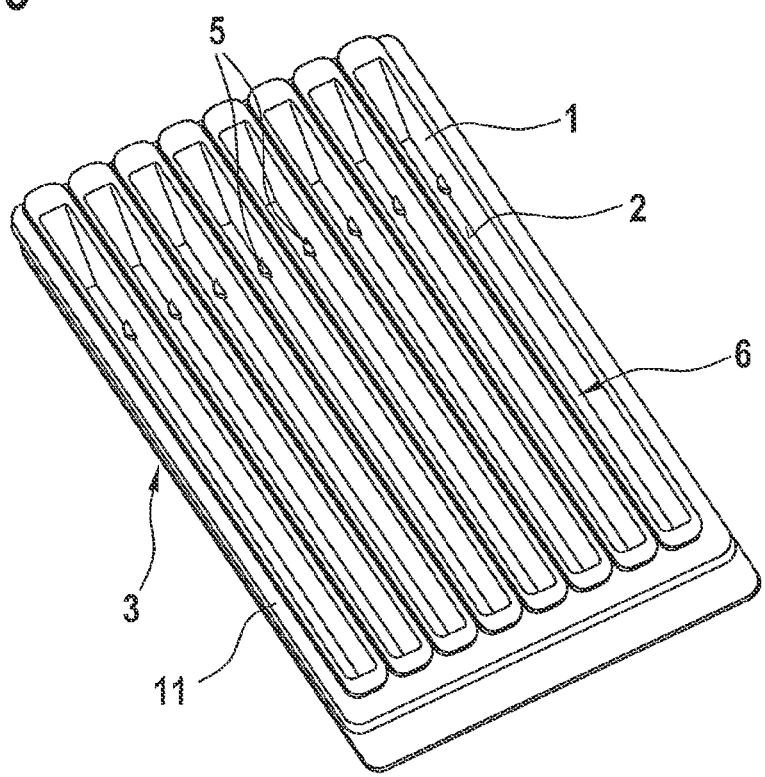
FIG. 5: A tray completely equipped with incubation channels.

Compared to FIG. 4, FIG. 5 shows a respectively shaped tray 3 completely equipped with incubation channels 1, eight in the example shown. In that, the incubation channels 1 are securely fixed within the tray of the tablet 3 by the webs 9 provided there.

The trays 3 shown in FIGS. 3, 4 and 5 enable, on the one hand, in a particularly simple manner, grouping of different immunoblot strips 6, and on the other hand, secure handling, in particular transport, fixing in automatic laboratory equipment, incubation and analysis, of a multitude of incubation channels 1 with the blot strips 6 arranged herein. In general, thus, a multitude of equal and/or different immunoblot strips 6 can be moved, processed and analyzed simultaneously, wherein it is likewise conceivable that the channels 1 are separated or connected with one another. Likewise, it is conceivable to stack the incubation channels 1 or a multitude of channels 1 and/or combine these into packaging units. In that, packaging units can be formed by arranging one or a multitude of incubation channels 1 with or without a tray 3 in packaging or covering the incubation channels 1 with the blot strips 6 arranged therein with a protective sheet.

The specification incorporates by reference the disclosure of German Patent Application DE 20 2012 004 404.4, filed May 3, 2012.

LIST OF REFERENCE NUMBERS

1 Incubation channel
2 Channel base
3 Rack
4 Take-up
5 Holding element
6 Immunoblot strip
7 Agitating equipment
8 Transverse axis
9 Web
10 Platform
11 Fastening element

The invention claimed is:

1. A device for incubating an immunoblot strip, comprising:
   at least one incubation channel having a channel base;
   an elongate immunoblot strip, wherein said immunoblot strip is insertable into said at least one incubation channel, wherein said immunoblot strip has a front surface and a back surface and has at least one biological material on the front surface, wherein said immunoblot strip is inserted with the back surface facing the channel base;
   an agitating equipment, wherein said immunoblot strip is agitatable around a transverse axis of the strip via said agitating equipment at least at times during incubation; and
   a rack for taking up at least two incubation channels and for handling and/or grouping incubation channels with immunoblot strips inserted wherein said rack comprises said at least one incubation channel which is oriented to hold liquid and, wherein said rack is in operative connection with said agitating equipment via load transmission points, wherein said take-ups are separated from one another at least in certain areas by webs, wherein the at least one incubation channel is clamped between adjacent webs to securely fix the at least one incubation channel, and wherein the at least one incubation channel is detachable from said take-ups without being destroyed.

2. The device according to claim 1, wherein said rack has fastening elements for placing said incubation channel in one of said take-ups or on a platform of automatic laboratory equipment.

3. The device according to claim 1, wherein said incubation channel has at least one holding element at the channel base for fixing said inserted immunoblot strip.

4. The device according to claim 1, wherein said immunoblot strip has a pressure sensitive adhesive on said back surface facing said channel base.

5. The device according to claim 1, wherein said at least one incubation channel is covered by a sheet.

6. The device according to claim 1, wherein at least two incubation channels are provided having a connection at respective longitudinal sides.

7. The device according to claim 6, wherein said connection and said at least two incubation channels are designed in one piece.

8. The device according to claim 1, wherein a total of at least two incubation channels are provided having a connection formed by a sheet covering said at least two incubation channels.

9. The device according to claim 6, wherein said connection has a diminished material strength relative to a material of said incubation channel and/or at least a recess to separate adjacent incubation channels from one another.

10. A method for incubating an immunoblot strip, comprising:
performing said method in the device according to claim 1;
providing at least one elongate immunoblot strip;
providing a biological material on a front surface of said at least one elongate immunoblot strip;
inserting said at least one elongate immunoblot strip into said incubation channel having said channel base, wherein a back surface of said immunoblot strip faces the channel base;
agitating said at least one elongate immunoblot strip around said transverse axis of the strip at least at times during incubation,
wherein at least two incubation channels with immunoblot strips located therein are inserted into take-ups of said rack configured to receive said take-ups, and wherein the rack, when equipped with incubation channels into which immunoblot strips are inserted, is connected with said agitating equipment such that said rack is agitated together with said incubation channels and
said immunoblot strips located therein at least at times during incubation.

11. The method according to claim 10, wherein said at least two immunoblot strips are clamped at said channel base of said incubation channel at least in certain areas.

12. The method according to claim 10, wherein said rack is positioned on a platform of said agitating equipment.

13. The device according to claim 6, wherein said connection has a diminished material strength relative to a material of said incubation channel and/or at least a perforation to separate adjacent incubation channels from one another.

* * * * *